United States Patent [19]

Bugner et al.

[11] Patent Number: 4,948,911

[45] Date of Patent: Aug. 14, 1990

[54] FLUORENONE DERIVATIVES

[75] Inventors: Douglas E. Bugner; Teh-Ming Kung; Louis J. Rossi, all of Rochester, N.Y.

[73] Assignee: Eastman Kodak Company, Rochester, N.Y.

[21] Appl. No.: 452,536

[22] Filed: Dec. 18, 1989

[51] Int. Cl.$^5$ ............................................. C07C 261/00
[52] U.S. Cl. .................................................. 558/427
[58] Field of Search ........................................ 558/427

[56] References Cited

U.S. PATENT DOCUMENTS

| | | | |
|---|---|---|---|
| 3,935,009 | 1/1976 | Crommentuyn et al. | 558/427 |
| 4,277,551 | 7/1981 | Sonnonstine et al. | 558/427 |
| 4,474,865 | 10/1984 | Ong et al. | 558/427 |
| 4,514,481 | 4/1985 | Scozzafava et al. | 558/427 |
| 4,546,059 | 10/1985 | Ong et al. | 558/427 |

OTHER PUBLICATIONS

*Chemical Abstracts,* Abstract No. 55:23461gh, Mien Chao and Pe-Ching Chao, "Friedal-Crafts Reaction of Fluorenone and 2-Nitrofluorenone with Arylsulfonyl Chlorides" (1957).

H. Kamogawa et al., "p-Styrenesulfinic Acid and Its Polymer as Reactants", *Bulletin of the Chemical Society of Japan,* vol. 52(10), pp. 3010–3014 (1979).

*Primary Examiner*—Mary C. Lee
*Assistant Examiner*—J. Richter
*Attorney, Agent, or Firm*—David F. Janci

[57] ABSTRACT

New chemical compounds are derivatives of fluorenones and are useful as electron-transport agents in electrophotographic elements.

3 Claims, No Drawings

FLUORENONE DERIVATIVES

FIELD OF THE INVENTION

This invention relates to certain chemical compounds, which are derivatives of fluorenones. The chemical compounds can be relatively efficiently and simply prepared; they have good solubility or dispersibility in organic solvents and polymeric binders; and they exhibit unexpectedly good properties when used as electron-transport agents in electrophotographic elements.

BACKGROUND

In electrophotography an image comprising a pattern of electrostatic potential (also referred to as an electrostatic latent image), is formed on a surface of an electrophotographic element comprising at least an insulative photoconductive layer and an electrically conductive substrate. The electrostatic latent image is usually formed by imagewise radiation-induced discharge of a uniform potential previously formed on the surface. Typically, the electrostatic latent image is then developed into a toner image by contacting the latent image with an electrographic developer. If desired, the latent image can be transferred to another surface before development.

In latent image formation the imagewise discharge is brought about by the radiation-induced creation of electron/hole pairs, which are generated by a material (often referred to as a charge-generation material) in the electrophotographic element in response to exposure to the imagewise actinic radiation. Depending upon the polarity of the initially uniform electrostatic potential and the type of materials included in the electrophotographic element, either the holes or the electrons that have been generated migrate toward the charged surface of the element in the exposed areas and thereby cause the imagewise discharge of the initial potential. What remains is a non uniform potential constituting the electrostatic latent image.

Many electrophotographic elements currently in use are designed to be initially charged with a negative polarity. Such elements contain material which facilitates the migration of positive holes toward the negatively charged surface in imagewise exposed areas in order to cause imagewise discharge. Such material is often referred to as a hole transport agent. In elements of that type a positively charged toner material is then used to develop the remaining imagewise unexposed portions of the negative polarity potential (i.e., the latent image) into a toner image. Because of the wide use of negatively charging elements, considerable numbers and types of positively charging toners have been fashioned and are available for use in electrographic developers. Conversely, relatively few high quality negatively charging toners are available.

However, for some applications of electrophotography it is more desirable to be able to develop the surface areas of the element that have been imagewise exposed to actinic radiation, rather than those that remain imagewise unexposed. For example, in laser printing of alphanumeric characters it is more desirable to be able to expose the relatively small percentage of surface area that will actually be developed to form visible alphanumeric toner images, rather than waste energy exposing the relatively large percentage of surface area that will constitute undeveloped background portions of the final image. In order to accomplish this while still employing widely available high quality positively charging toners, it is necessary to use an electrophotographic element that is designed to be positively charged. Thus, positive toner can then be used to develop the exposed surface areas (which will have relatively negative electrostatic potential after exposure and discharge, compared to the unexposed areas, where the initial positive potential will remain).

An electrophotographic element designed to be initially positively charged should, however, contain an adequate electron-transport agent (i.e., a material which adequately facilitates the migration of photo-generated electrons toward the positively charged insulative element surface). Unfortunately (and analogous to the situation with positive and negative toners), many materials having good hole-transport properties have been fashioned for use in electro-photographic elements, but relatively few materials are known to provide good electron-transport properties in electrophotographic elements.

A number of chemical compounds having electron-transport properties are described, for example, in U.S. Pat. Nos. 4,175,960; 4,514,481; 4,474,865; 4,546,059; 4,277,551; and 4,609,602. However, many prior art compounds have one or more drawbacks.

Some prior art electron-transport agents do not perform the electron-transporting function very well, especially under certain conditions or when included in certain types of electrophotographic elements. Also, some cause an undesirably high rate of discharge of the electrophotographic element before it is exposed to actinic radiation (often referred to as high dark decay).

Some prior art electron-transport compounds are not soluble or dispersible or have relatively limited solubility or dispersibility in coating solvents of choice or in some polymeric binders desired to be used in charge-transport layers, such that attempts to include sufficient amounts of such electron-transport agents in electrophotographic elements result in some crystallization of the electron-transport agents, which in turn causes problems such as undesirable levels of dark decay and such as unwanted scatter or absorption of actinic radiation intended to pass undisturbed through the charge transport layer to a radiation sensitive portion of the element.

Also, some known electron-transport agents comprise compounds known to be toxic or carcinogenic (e.g., 2,4,7-trinitrofluorenone).

Furthermore, some electron-transport agents suffer from being obtainable only through difficult, lengthy, and/or otherwise relatively inefficient or uneconomical methods of preparation.

In general, there are simply not enough known relatively good electron-transport agents available to choose from in order to have the flexibility to be able to develop electrophotographic elements that photodischarge by means of electron-transport and that can be optimized for use in various different situations (e.g., where an element is desired to contain certain charge-generating materials, sensitizers, binders, conducting layers, etc., or where it is desired to charge the element with a certain polarity or level of charge, to subject the element to imagewise exposure at a particular wavelength or intensity of radiation, to use the element in copiers that require it to photodischarge at a certain speed or require it to be able to hold a charge in darkness for a particular period of time before imagewise exposure, etc.).

Thus, there is a continuing need for new chemical compounds that will exhibit good electron-transport properties in electrophotographic elements without imparting undesirably poor dark decay properties thereto, in order to have the flexibility to meet the above noted needs. The chemical compounds should be sufficiently soluble or dispersible in coating solvents and polymeric binders of choice, and should be capable of being readily prepared by relatively simple and efficient methods.

SUMMARY OF THE INVENTION

The present invention meets the above-noted need by providing new chemical compounds that have good utility as electron-transport agents in electrophotographic elements, thus broadening the assortment of such agents available for selection for optimum performance in various situations. The new chemical compounds are derivatives of fluorenones and have the structure

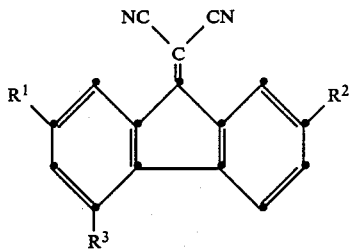

wherein:

$R^1$, $R^2$, and $R^3$ are each independently hydrogen, nitro, alkyl, or —$SO_2R^4$, with the proviso that at least one of $R^1$, $R^2$, and $R^3$ is —$SO_2R^4$;

each $R^4$ is independently alkyl, aryl, alkaryl, alkoxyaryl, or haloaryl;

each alkyl or alkoxy moiety recited above has from 1 to 8 carbon atoms; and each aryl moiety recited above has from 6 to 10 aromatic ring carbon atoms.

The chemical compounds of the invention can be readily prepared by relatively simple and efficient methods. They have good solubility or dispersibility in many coating solvents and in many film-forming polymeric binders that are useful to form one or more layers in electrophotographic elements. In electrophotographic elements, the chemical compounds serve as electron-transport agents with good capability of accepting and transporting electrons generated by radiation-activated charge-generation materials in the elements, and they do not impart unacceptably high dark decay characteristics to the elements.

It should be noted that electrophotographic elements, containing electron-transport agents comprising the chemical compounds of this invention, are described and claimed in copending U.S. patent application No. 07/452,533, filed of even date herewith.

DESCRIPTION OF PREFERRED EMBODIMENTS

The chemical compounds of Structure (I) of the invention can be conveniently and efficiently prepared from readily available starting materials.

For example, fluorene can be reacted with 2,4,6-triisopropylbenzenesulfonyl chloride in the presence of aluminum chloride to yield 2 (2,4,6-tri-isopropylphenylsulfonyl)fluorene, which can be refluxed with sodium dichromate dihydrate in glacial acetic acid to yield 2 (2,4,6-triisopropylphenyl sulfonyl)fluorenone, which in turn can be refluxed with malononitrile in methanol in the presence of piperidine to yield 2 (2,4,6-triisopropylphenylsulfonyl)-9-(dicyanomethylene)fluorene.

Also, for example, 2,7-bis(chlorosulfonyl)-fluorenone can be mixed with a heated solution of sodium bicarbonate and sodium sulfite in water to yield 2,7-bis(sodiosulfonyl)fluorenone, which can be refluxed with n-butyl iodide in ethanol to yield 2,7-bis(n-butylsulfonyl)fluorenone, which in turn can be refluxed with malononitrile in methanol in the presence of piperidine to yield 2,7-bis(n-butyl sulfonyl)-9-(dicyanomethylene)fluorene.

Further details of specific compound preparations are described below.

While any of the specific compounds of the invention encompassed by generic Structure (I) can be employed in electrophotographic elements, some are preferred over others in given situations. For example, while any compound in accordance with Structure (I) can be adequately dissolved or dispersed along with an appropriate polymeric film-forming binder in a solvent such as acetonitrile or dimethylsulfoxide and can then be solvent-coated on an appropriate substrate to form a charge-transport layer, if it is desired to coat from solvents such as dichloromethane or trichloroethylene, instead, then it is preferred to employ a Structure (I) compound that is structurally asymmetric (as used herein in regard to Structure (I), the phrase, "structurally asymmetric", is intended to mean that $R^1$ and $R^2$ are not identical moieties, and/or that $R^3$ is not hydrogen). Such structurally asymmetric Structure (I) compounds are more soluble in coating solvents such as dichloromethane than structurally symmetric Structure (I) compounds and can therefore be incorporated at higher concentrations in charge transport layers coated from such solvents. Such higher concentrations can be necessary in some instances (depending upon the nature of the rest of the electrophotographic element, the photodischarge speed required, etc.) in order to achieve desired performance of the element.

Some specific examples of Structure (I) compounds of the invention, that have been prepared eleotrophotographic elements, are listed in Table I below along with their half-wave reduction potentials (as measured in volts at a Pt electrode at 25° C. at a concentration of about 1 mM in dichloromethane vs. a saturated calomel electrode; ferrocene was used as an internal standard and was found to exhibit a half-wave reduction potential of +0.458±0.008V over 20 measurements under these conditions). While half-wave reduction potential cannot be used as a reliable predictor of good performance as an electron-transport agent, it has been observed that most chemical compounds that are known to be practically useful as electron-transport agents have reduction potentials in the range of about 0 to −1V. The compounds in Table I are described with reference to Structure (I).

TABLE I

| Compound | R¹ | R² | R³ | Reduction Potential (V) |
|---|---|---|---|---|
| I-A | 2,4,6-triisopropyl-phenylsulfonyl | H | H | −0.55 |
| I-B | n-butylsulfonyl | n-butylsulfonyl | H | −0.37 |
| I-C | p-chlorophenylsulfonyl | p-chlorophenylsulfonyl | H | −0.36 |
| I-D | p-tolylsulfonyl | p-tolylsulfonyl | H | −0.39 |
| I-E | p-methoxyphenylsulfonyl | p-methoxyphenylsulfonyl | H | −0.39 |
| I-F | phenylsulfonyl | phenylsulfonyl | H | −0.38 |
| I-G | p-t-butylphenylsulfonyl | p-t-butylphenylsulfonyl | H | −0.40 |
| I-H | H | p-t-butylphenylsulfonyl | p-t-butylphenylsulfonyl | −0.39 |
| I-J | 2,4,6-triisopropyl-phenylsulfonyl | p-methoxyphenylsulfonyl | H | −0.41 |
| I-K | p-methoxyphenylsulfonyl | nitro | H | −0.35 |
| I-L | t-butyl | p-methoxyphenylsulfonyl | p-methoxyphenyl-sulfonyl | −0.43 |

The new chemical compounds of the invention are useful in electrophotographic elements of various types, all of which contain one or more of the chemical compounds of Structure (I) described above to serve as electron-transport agents in the elements. The various types of elements include those commonly referred to as multiactive (also referred to as multilayer or multi-active-layer) elements.

Multiactive elements are so named, because they contain at least two active-layers, at least one of which is capable of generating charge (i.e., electron/hole pairs) in response to exposure to actinic radiation and is referred to as a charge-generation layer (hereinafter also referred to as a CGL), and at least one of which is capable of accepting and transporting charges generated by the charge-generation layer and is referred to as a charge-transport layer (hereinafter also referred to as a CTL). Such elements typically comprise at least an electrically conductive layer, a CGL, and a CTL. Either the CGL or the CTL is in electrical contact with both the electrically conductive layer and the remaining CGL or CTL. The CGL contains at least a charge-generation material; the CTL contains at least a charge-transport agent; and either or both layers can contain an electrically insulative film-forming polymeric binder. In multiactive elements utilizing compounds of the invention the charge-transport agent is an electron-transport agent comprising one of the inventive chemical compounds of Structure (I) described above.

Structure (I) compounds may also be useful as electron-transport agents in electrophotographic elements referred to as single active-layer or single layer elements. Single active-layer elements are so named, because they contain only one layer that is active both to generate and to transport charges in response to exposure to actinic radiation. Such elements typically comprise at least an electrically conductive layer in electrical contact with a photoconductive layer. In single-active-layer elements utilizing compounds of the invention, the photoconductive layer contains a charge-generation material to generate electron/hole pairs in response to actinic radiation and an electron-transport material, comprising one or more of the inventive chemical compounds of Structure (I) described above, which is capable of accepting electrons generated by the charge-generation material and transporting them through the layer to effect discharge of the initially uniform electrostatic potential. The photoconductive layer is electrically insulative, except when exposed to actinic radiation, and sometimes contains an electrically insulative polymeric film-forming binder, which may itself be the charge generating material or may be an additional material which is not charge-generating. In either case the electron-transport agent is dissolved or dispersed as uniformly as possible in the binder film.

Single-active-layer and multiactive electrophotographic elements and their preparation and use, in general, are well known and are described in more detail, for example, in U.S. Pat. Nos. 4,701,396; 4,666,802; 4,578,334; 4,719,163; 4,175,960; 4,514,481; and 3,615,414, the disclosures of which are hereby incorporated herein by reference. The only essential difference of electrophotographic elements utilizing compounds of the present invention from generally known elements is that the new elements contain chemical compounds of Structure (I) as electron-transport agents.

In preparing single active-layer electrophotographic elements containing compounds of the invention, the components of the photoconductive layer, including any desired addenda, can be dissolved or dispersed together in a liquid and can be coated on an electrically conductive layer or support. The liquid is then allowed or caused to evaporate from the mixture to form the permanent layer containing from about 10 to about 70 percent (by weight) of the inventive electron-transport agent and from about 0.01 to about 50 weight percent of the charge generating material. Included among many useful liquids for this purpose are, for example, aromatic hydrocarbons such as benzene, toluene, xylene and mesitylene; ketones such as acetone and butanone; halogenated hydrocarbons such as methylene chloride, trichloroethane, chloroform and ethylene chloride; ethers, including ethyl ether and cyclic ethers such as tetrahydrofuran; other solvents such as acetonitrile and dimethylsulfoxide; and mixtures thereof.

In preparing multiactive electrophotographic elements containing compounds of the invention, the components of the CTL can be similarly dissolved or dispersed in such a liquid coating vehicle and can be coated on either an electrically conductive layer or support or on a CGL previously similarly coated or otherwise formed on the conductive layer or support. In the former case a CGL is thereafter coated or otherwise formed (e.g., by vacuum-deposition) on the CTL. The CTL will usually contain from about 10 to about 70 weight percent of the inventive electron-transport agent, although concentrations outside that range may be found to be useful in some cases.

Various electrically conductive layers or supports can be employed in electrophotographic elements containing compounds of the invention, such as, for example, paper (at a relative humidity above 20 percent); aluminum-paper laminates; metal foils such as aluminum foil, zinc foil, etc.; metal plates such as aluminum, copper, zinc, brass and galvanized plates; vapor deposited metal layers such as silver, chromium, vanadium, gold, nickel, aluminum and the like; and semiconductive layers such as cuprous iodide and indium tin oxide. The metal or semiconductive layers can be coated on paper or conventional photographic film bases such as poly(ethylene terephthalate), cellulose acetate, polystyrene, etc. Such conducting materials as chromium, nickel, etc. can be vacuum deposited on transparent film supports in sufficiently thin layers to allow electrophotographic elements prepared therewith to be exposed from either side.

Any charge-generation material can be utilized in elements that contain an electron-transport agent comprising a compound of the invention. Such materials include inorganic and organic (including monomeric, metallo-organic and polymeric organic) materials, for example, zinc oxide, lead oxide, selenium, phthalocyanine, perylene, arylamine, polyarylalkane, and polycarbazole materials, among many others.

When solvent coating a photoconductive layer of a single-active-layer element or a CGL and/or CTL of a multiactive element, a film-forming polymeric binder can be employed. The binder may, if it is electrically insulating, help to provide the element with electrically insulating characteristics. It also is useful in coating the layer, in adhering the layer to an adjacent layer, and when it is a top layer, in providing a smooth, easy to clean, wear resistant surface.

The optimum ratio of charge-generation or charge-transport material to binder may vary widely depending on the particular materials employed. In general, useful results are obtained when the amount of active charge-generation and/or charge-transport material contained within the layer is within the range of from about 0.01 to about 90 weight percent, based on the dry weight of the layer.

Representative materials which can be employed as binders in charge-generation and charge-transport layers are film-forming polymers having a fairly high dielectric strength and good electrically insulating properties. Such binders include, for example, styrene-butadiene copolymers; vinyl toluene-styrene copolymers; styrene-alkyd resins; silicone-alkyd resins; soya-alkyd resins; vinylidene chloride-vinyl chloride copolymers; poly(vinylidene chloride); vinylidene chloride-acrylonitrile copolymers; vinyl acetate vinyl chloride copolymers; poly(vinyl acetals), such as poly(vinyl butyral); nitrated polystyrene; poly(methylstyrene); isobutylene polymers; polyesters, such as poly[ethylene-co-alkylenebis(alkyleneoxyaryl) phenylenedicarboxylate]; phenolformaldehyde resins; ketone resins; polyamides; polycarbonates; polythiocarbonates; poly[ethylene-co-isopropylidene-2,2-bis(ethyleneoxyphenylene)terephthalate]; copolymers of vinyl haloacrylates and vinyl acetate such as poly(vinyl m-bromobenzoate-co-vinyl acetate), chlorinated poly(olefins), such as chlorinated poly(ethylene); and polyimides, such as poly[1,1,3-trimethyl-3-(4'-phenyl)-5-indane pyromellitimide].

Binder polymers should provide little or no interference with the generation or transport of charges in the layer. Examples of binder polymers which are especially useful include bisphenol A polycarbonates and polyesters such as poly[4,4'-(norbornylidene)diphenylene terephthalate-co-azelate].

CGL's and CTL's can also optionally contain other addenda such as leveling agents, surfactants, plasticizers, sensitizers, contrast-control agents, and release agents, as is well known in the art.

Also, elements containing a compound of the invention can contain any of the optional additional layers known to be useful in electrophotographic elements in general, such as, e.g., subbing layers, overcoat layers, barrier layers, and screening layers.

The following examples are presented to further illustrate the preparation of some specific compounds of the invention and their utility as electron-transport agents in various electrophotographic elements.

EXAMPLE 1

Compound I-A of Table I was prepared as follows.

The reaction was carried out under an argon atmosphere in a 500-ml, 3-necked, round-bottom flask equipped with a magnetic stirrer, reflux condenser, and an addition funnel. A mixture of 2,4,6-triisopropylbenzenesulfonyl chloride (60.6 g, 200 mmol) and $AlCl_3$ (27.1 g, 203 mmol) in dichloromethane (DCM; 200 ml) was heated to reflux, and a solution of fluorene (16.1 g, 96.9 mmol) in DCM (100 ml) was added dropwise over 30 minutes. The mixture was refluxed for 87 hours, then was cooled and cautiously poured into 1N HCl (960 ml). The organic phase was drawn off, and the aqueous phase was extracted with additional DCM. The combined DCM phases were evaporated to dryness, yielding 88.3 g of a brown oil which solidified on standing. The product was triturated with cyclohexane (500 ml) at room temperature, and a finely divided off-white solid was collected by filtration. The filter cake was washed with additional cyclohexane, then dried in a vacuum oven. The filtrate deposited additional solids which were collected, washed, and dried. Thin layer chromatography of both solid products exhibited single spots of identical $R_f$. Analytical data (from infrared (IR) spectroscopy, nuclear magnetic resonance (NMR) spectroscopy, field desorption mass spectrometry (FDMS), and combustion analysis) indicate this product to be 2-(2,4,6-triisopropylphenylsulfonyl)fluorene.

Total yield: 40.0 g (92.4 mmol, 95.4%).

Melting point: 164.6°–165.5° C.

Elemental analysis: calculated for $C_{28}H_{32}O_2S$: 77.7% C, 7.5% H, and 7.4% S; found: 76.3% C, 7.4% H, and 7.2% S.

A portion of the 2-(2,4,6-triisopropylphenylsulfonyl)fluorene just described (8.67 g, 20.0 mmol) was placed in a 1 liter flask (equipped with a magnetic stirrer and reflux condenser) along with 17.9 g (60.0 mmol, 3.0 eq) of sodium dichromate dihydrate and 500 ml of glacial acetic acid. The mixture was refluxed for 15 hours, cooled, and poured into 2.0 liters of water. The solids were collected by filtration and washed with additional water (2×1.0 liter). The crude product was dried and purified by chromatography. A total of 3.60 g (8.06 mmol, 40.3%) of pure 2-(2,4,6-triisopropylphenylsulfonyl)fluorenone was obtained in this manner. Its structure was confirmed by IR, NMR, and ultraviolet-visible (UV-VIS) spectroscopy, FDMS, and combustion analysis.

Melting point: 229.6°–230.9° C.

Elemental analysis: calculated for $C_{28}H_{30}SO_3$: 75.3% C, 6.8% H, and 7.2% S; found: 74.4% C, 6.7% H, and 7.1% S.

To a suspension of 6.51 g (14.6 mmol) of 2-(2,4,6-triisopropylphenylsulfonyl)fluorenone in abs. MeOH (250 ml) were added 2.5 ml (40 mmol) of malononitrile and 20 drops of piperidine. The stirred mixture was refluxed under nitrogen for 4.5 hours, then cooled. The orange crystalline solid was collected by filtration and rinsed well with MeOH. The product (Compound I-A of Table I) was further purified by chromatography to remove traces of unreacted fluorenone precursor. Total yield after chromatography: 5.51 g (11.1 mmol, 76.3%). The product structure was confirmed by IR, NMR, and UV-VIS spectroscopy, FDMS, and combustion analysis.

Melting point: 251.7°–252.8° C.

Elemental analysis: calculated for $C_{31}H_{30}N_2SO_2$: 75.3% C, 6.1% H, 5.7% N, and 6.5% S; found: 74.8% C, 6.1% H, 5.7% N, and 6.2% S.

EXAMPLE 2

Compound I-B of Table I was prepared as follows.

2,7-Bis(chlorosulfonyl)fluorenone was prepared by a modification of the procedure of A. Chrzqszczewskla and T. Machlanski, *Lodz. Tow. Nauk. Soc. Sci. Lodz. Acta Chim.*, 11, 143 (1966); (CA 66:37089v).

A solution of sodium bicarbonate (8 9 g, 106 mmol) and sodium sulfite (12.6 g, 99.5 mmol) in water (40 ml) was stirred and heated to 75+±5+ C. 2,7-Bis(chlorosulfonyl)fluorenone (10.0 g, 26.5 mmol) was added in portions over 1.5 hours while maintaining the temperature at 75°±5° C. Additional water (20 ml) was used to rinse down the sides of the beaker occasionally during the addition. The mixture was cooled and stirred overnight at room temperature. A precipitate which formed was collected by filtration, and the filtrate was concentrated to ca. 50 ml. Upon cooling, the filtrate yielded a second crop of crystals which were also collected by filtration. IR analysis of both fractions indicated that the second fraction was consistent with 2,7-bis(sodiosulfonyl)fluorenone. The damp solid second fraction (ca. 18 g) was used without further treatment It was placed in a 250-ml round bottom flask equipped with a magnetic stirrer and a reflux condenser. Ethanol (100 ml) was added, and the suspension was refluxed. n-Butyl iodide (16.6 ml, 146 mmol) was then added in one portion, and refluxing was continued for 18 hours. The reaction mixture was chilled in ice water, and the solids were collected by filtration, washing with additional ice water. The solids were dried, dissolved in DCM, and filtered to remove any insoluble material. The DCM was evaporated, yielding 3.7 g (8.80 mmol, 33.2%) of 2,7-bis(n-butylsulfonyl)fluorenone. The product structure was confirmed by IR and NMR spectroscopy, FDMS, and combustion analysis.

Melting point: 229°–232° C. Elemental analysis: calculated for $C_{21}H_{24}S_2O_5$: 60.0% C, 5,8% H, and 15.2% S; found: 60.0% C, 5.6% H, and 15.5% S.

This fluorenone was converted to 2,7-bis(n-butylsulfonyl)-9-(dicyanomethylene)fluorene (Compound I-B of Table I) in good yield by the same procedure used to convert the fluorenone to its corresponding 9-(dicyanomethylene)fluorene in Example 1. Its structure was confirmed by elemental and spectroscopic analyses.

EXAMPLES 2-6

Compounds I-C, I-D, I-E, I-F, and I-G of Table I were prepared in a manner identical to that of Example 1, except that, instead of the 2,4,6-triisopropylbenzenesulfonyl chloride employed in Example 1, p-chlorobenzenesulfonyl chloride, p-toluenesulfonyl chloride, p-methoxybenzenesulfonyl chloride, benzenesulfonyl chloride, and p-t-butylbenzenesulfonyl chloride, respectively, were employed. Yields were good, and all structures were confirmed by elemental and spectroscopic analyses.

EXAMPLE 7

Compound I-H of Table I was prepared by isolating the byproduct, 2,5-bis(p-t-butylphenylsulfonyl)fluorenone, during the preparation of 2,7 -bis(p-t-butylphenylsulfonyl)fluorenone in Example 6, and then converting it to its corresponding 9-(dicyanomethylene)fluorene in the manner employed in Example 1. The structure of Compound I-H was confirmed by elemental and spectroscopic analyses.

EXAMPLES 8-10

Compounds I-J, I-K, and I-L of Table I were prepared by the procedure of Example 1, except that instead of fluorene, 2-(2,4,6-triisopropylphenylsulfonyl)fluorene, 2nitrofluorene, and 2-t-butylfluorene, respectively, were employed, and, instead of 2,4,6-triisopropylbenzenesulfonyl chloride, p-methoxybenzenesulfonyl chloride was used. The structures of Compounds I-J, I-K, and I-L were confirmed by elemental and spectroscopic analyses.

In the following Examples, the structure, preparation, and performance of various electrophotographic elements containing compounds within the scope of the present invention are illustrated. In the Examples performance is illustrated in regard to electrophotographic speed (also referred to as sensitivity) and dark decay properties.

In illustrating electrophotographic speed in the Examples, the element was electrostatically corona-charged to an initial positive potential (usually about 300–500 volts) and then exposed to actinic radiation (radiation having peak intensity at a wavelength to which the charge-generation material in the element is sensitive in order to generate electron/hole pairs) in an amount sufficient to photoconductively discharge a certain amount or percentage of the initial voltage (usually 100V and/or 50% of the initial voltage). Electrophoto-graphic speed was measured in terms of the amount of incident actinic radiant energy (expressed in ergs/cm$^2$) needed to achieve the desired amount or percentage of discharge of the initial voltage. The lower the amount of radiation needed to achieve the desired degree of discharge, the higher is the electrophotographic speed of the element, and vice versa.

In illustrating dark decay properties in the Examples, the rate of dissipation of the initial voltage (expressed in V/s, i.e., volts per second) was measured while the element remained in darkness (i.e., before any exposure to actinic radiation). This was accomplished by measuring the initial voltage and the voltage remaining on the element after 2 seconds in darkness and dividing the difference by 2. The lower the rate of discharge in darkness, the better is the dark decay property of the element, i.e., the better is the element's ability to retain its initial potential before exposure.

In the tables of performance data in the Examples, "Electron-transport agent", refers to the chemical compound of the invention incorporated in the CTL of an electrophotographic element to serve as an electron-transport agent, and the compound is identified with reference to its designation in Table I above. "Wt %"

refers to the percent by weight of electron-transport agent employed, based on the total weight of polymeric binder and electron-transport agent included in the solution used to coat the CTL of the element. "$V_o$3[ refers to the uniform positive potential (in volts) on the element, after it was charged by corona-charging and after any dark decay; such potential having been measured just prior to any exposure of the element to actinic radiation. "DD3[ refers to the rate of dark decay of the element, prior to exposure to actinic radiation, measured in volts per second (V/s) as described above. "$E(V_o100)$" refers to the amount of incident actinic radiant energy (expressed in ergs/cm$^2$) that was needed to discharge the element to a level 100 volts below $V_o$. "$E(50\% V_o)$" refers to the amount of incident actinic radiant energy (expressed in ergs/cm$^2$) that was needed to discharge the element to a level of 50% of $V_o$.

EXAMPLES 11-15

Electrophotographic elements containing various concentrations of inventive electron-transport agents in their CTL's were prepared as follows.

A conductive layer-coated support was prepared by vacuum-depositing a thin conductive layer of aluminum onto a 178 micrometer thickness of poly(ethylene terephthalate) film.

A charge-generation layer (CGL) was prepared by dispersing the charge-generation material, titanyl tetrafluorophthalocyanine (described more extensively in U.S. Pat. No. 4,701,396), in a solution of a polymeric binder, comprising a polyester formed from 4,4'-(2-norbornylidene)diphenol and terephthalic acid:azelaic acid (40:60 molar ratio), in dichloromethane (the weight ratio of charge-generation material:binder being 2:1), ball milling the dispersion for 60 hours, diluting with a mixture of dichloromethane (DCM) and 1,1,2-trichloroethane (TCE) (to yield a final DCM:TCE weight ratio of 80:20) to achieve suitable coating viscosity, coating the dispersion onto the conductive layer, and drying off the solvent to yield a CGL of 0.5 micrometer thickness.

A coating solution for forming a charge-transport layer (CTL) was then prepared comprising 10 weight percent solids dissolved in dichloromethane. The solids comprised the inventive electron-transport agent, Compound I-A, prepared as in Example 1 above and a polymeric binder comprising a polyester formed from 4,4'-(2-norbornylidene)diphenol and terephthalic acid:azelaic acid (40:60 molar ratio). The concentration of electron-transport agent was different for each Example, as noted in Table II. The solution was then coated onto the CGL and dried to form the CTL on the CGL. The combined thickness of CGL and CTL was in the range of 7 to 10 micrometers.

Each of the resultant electrophotographic elements was then corona-charged to a uniform positive potential.

Dark decay rate of the initial potential was measured for each element.

Each of the uniformly charged elements was subjected to simulated imaging exposure by exposing it through the outer surface of the CTL to radiation having a wavelength of about 800 nanometers (nm) (to which the charge-generation material is sensitive, in order to generate electron/hole pairs in the CGL) at a rate of 3.7 ergs of radiant energy per square centimeter of element surface per second (3.7 ergs/cm$^2$s), and E(-$V_o$-100) and E(50% $V_o$) were measured for each element.

Results are presented in Table II.

TABLE II

| Example | Electron-transport agent | Wt. % | $V_o$ (V) | DD (V/s) | $E(V_o$-100) (ergs/cm$^2$) | $E(50\% V_o)$ (ergs/cm$^2$) |
|---|---|---|---|---|---|---|
| 11 | I-A | 20 | 508 | 1.5 | 29.0 | * |
| 12 | I-A | 30 | 506 | 3.9 | 4.7 | 30.5 |
| 13 | I-A | 40 | 498 | 0.7 | 3.7 | 15.1 |
| 14 | I-A | 50 | 499 | 4.2 | 3.5 | 12.3 |
| 15 | I-A | 60 | # | # | # | # |

\* = The potential did not reach 50% $V_o$ by photodischarge.
# = The electron-transport agent began to crystallize out of the CTL coating; no tests were performed.

The data in Table II show that an excellent element can be fashioned with inventive Compound I-A. Element performance improved with increasing concentration of electron-transport agent (Ex's 11-14), up to the point where the agent began to crystallize out of the CTL (Ex. 5). Optimum performance occurs when such an element contains Compound I-A in the CTL at somewhere between 40 and 60 weight %.

EXAMPLES 16-20

Electrophotographic elements were prepared and tested as in Examples 11-15, except that various electron-transport agents (inventive Compounds from Table I) were included in the CTL's at various concentrations. Imaging exposure was carried out at a rate of 3.0 ergs/cm$^2$s with radiation having a wavelength of about 820 nm.

Results are presented in Table III.

TABLE III

| Example | Electron-transport agent | Wt. % | $V_o$ (V) | DD (V/s) | $E(50\% V_o)$ (ergs/cm$^2$) |
|---|---|---|---|---|---|
| 16 | I-A | 43 | 300 | 1 | 21.3 |
| 17 | I-G | 30 | 302 | 0 | * |
| 18 | I-G | 54 | # | # | # |
| 19 | I-H | 30 | 290 | 3 | 23.4 |
| 20 | I-H | 54 | 295 | 2 | 18.3 |

= These Wt. %'s represent equimolar concentrations of 0.87 mmol/g.
\* = The potential did not reach 50% $V_o$ by photodischarge.
# = The electron-transport agent was not sufficiently soluble in the CTL coating solution of binder in dichloromethane; no tests were performed.

The data in Table III illustrate good performance, except in the case of symmetrically structured Compound I-G, which was not soluble enough in the dichloromethane coating solution to achieve a concentration high enough to yield sufficient performance. Such high enough concentration can be achieved by employing, instead, a coating solvent such as acetonitrile or dimethylsulfoxide, in which Compound I-G is more soluble.

Note also that at equal molar concentrations Compound I-H (having two sulfonyl substituents) afforded better electrophotographic speed (lower $E(50\% V_o)$) than Compound I-A (having only one sulfonyl substituent).

EXAMPLES 21-25

Examples 16-20 were repeated, except that the elements contained a different conductive layer and charge-generation layer.

Instead of the aluminum conductive layer, a thin conductive layer of nickel was vacuum deposited on the polyester support.

Instead of the CGL comprising a phthalocyanine in binder, CGL's in the elements of Examples 21-25 were formed by evaporation-deposition of selenium charge-generation material onto the conductive layer to form a CGL of about 0.4 micrometer thickness.

Imaging exposure was carried out at a rate of 3.0 ergs/cm$^2$s with radiation having a wavelength of about 500 nm (to which the selenium charge-generation material is sensitive in order to generate electron/hole pairs in the CGL).

Results are presented in Table IV.

TABLE IV

| Example | Electron-transport agent | Wt. % | $V_o$ (V) | DD (V/s) | E(50% $V_o$) (ergs/cm$^2$) |
|---|---|---|---|---|---|
| 21 | I-A | 43 ✔ | 302 | 0 | 31 |
| 22 | I-G | 30 | 300 | 4 | * |
| 23 | I-G | 54 ✔ | # | # | # |
| 24 | I-H | 30 | 310 | 0 | * |
| 25 | I-H | 54 ✔ | 310 | 1 | 23 |

✔ = These wt. %'s represent equimolar concentrations of 0.87 mmol/g.
\* = The potential did not reach 50% $V_o$ by photodischarge.
\# = The electron transport agent was not sufficiently soluble in the CTL coating solution of binder in dichloromethane; no tests were performed.

The comments made above after Table III apply equally as well to the results in Table IV.

The invention has been described in detail with particular reference to certain preferred embodiments thereof, but it should be appreciated that variations and modifications can be effected within the spirit and scope of the invention.

What is claimed is:

1. A chemical compound having the structure

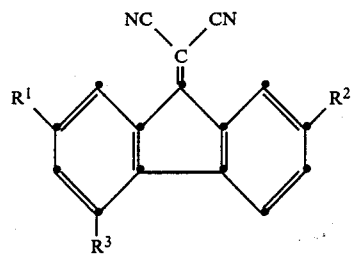

wherein:
$R^1$, $R^2$, and $R^3$ are each independently hydrogen, nitro, alkyl, or —SO$_2$R$^4$, with the proviso that at least one of $R^1$, $R^2$, and $R^3$ is —SO$_2$R$^4$;
each R$^4$ is independently alkyl, aryl, alkaryl, alkoxyaryl, or haloaryl;
each alkyl or alkoxy moiety recited above has from 1 to 8 carbon atoms; and
each aryl moiety recited above has from 6 to 10 aromatic ring carbon atoms.

2. The chemical compound of claim 1, wherein $R^1$, $R^2$, and $R^3$ are moieties such that the chemical compound is structurally asymmetric.

3. The chemical compound of claim 1, wherein:
$R^1$ is —SO$_2$R$^4$, $R^2$ and $R^3$ are
$R^1$ is —SO$_2$R$^4$, $R^2$ and $R^3$ are hydrogen, and $R^4$ is 2,4,6-triisopropylphenyl, or
$R^1$ is hydrogen, $R^2$ and $R^3$ are —SO$_2$R$^4$, and $R^4$ is p-t-butylphenyl.

* * * * *